United States Patent
Lubda et al.

(10) Patent No.: US 7,235,199 B2
(45) Date of Patent: Jun. 26, 2007

(54) METHOD FOR PRODUCING MONOLITHIC CHROMATOGRAPHY COLUMNS

(75) Inventors: Dieter Lubda, Bensheim (DE); Egbert Mueller, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 526 days.

(21) Appl. No.: 10/297,992

(22) PCT Filed: May 16, 2001

(86) PCT No.: PCT/EP01/05540

§ 371 (c)(1),
(2), (4) Date: Dec. 12, 2002

(87) PCT Pub. No.: WO01/96858

PCT Pub. Date: Dec. 20, 2001

(65) Prior Publication Data

US 2003/0155676 A1    Aug. 21, 2003

(30) Foreign Application Priority Data

Jun. 14, 2000 (DE) ................................ 100 28 447

(51) Int. Cl.
*B29C 67/20* (2006.01)
*B01D 15/00* (2006.01)
(52) U.S. Cl. ........................ 264/46.9; 264/656; 210/656
(58) Field of Classification Search .................. 264/41, 264/42, 46.4, 46.6, 46.9, 656; 210/656, 510.1, 210/198.2
See application file for complete search history.

(56) References Cited

U.S. PATENT DOCUMENTS

| 5,624,875 | A | * | 4/1997 | Nakanishi et al. | ............ | 501/39 |
| 5,679,255 | A | * | 10/1997 | Cortes et al. | ................ | 210/656 |
| 6,395,183 | B1 | * | 5/2002 | Valaskovic et al. | ......... | 210/656 |
| 6,758,966 | B2 | * | 7/2004 | Myers | ..................... | 210/198.2 |

FOREIGN PATENT DOCUMENTS

| WO | WO 9503256 | 2/1995 |
| WO | WO 9859238 | 12/1998 |
| WO | WO 99/50654 | * 10/1999 |

OTHER PUBLICATIONS

Ishizuka et al, Performance of a Monolithic Silica Column in a Capillary under Presure-Driven and Electrodriven Conditions, Analytical Chemistry vol. 72, No. 6 Mar. 15,200,Published on the web Feb. 10, 2000, pp. 1275-1280.*

Ishizuka N et al., "Designing monolithic double-pore silica for high-speed liquid chromatography," Journal of Chromatography, vol. 797, No. 1-2, pp. 133-137, Feb. 1998.

Tang Q et al., "Column technology for capillary electrochromatography," TRAC, Trends in Analytical Chemistry, vol. 19, No. 11, pp. 648-663, Nov. 2000.

* cited by examiner

*Primary Examiner*—Carlos Lopez
(74) *Attorney, Agent, or Firm*—Millen, White, Zelano & Branigan, P.C.

(57) ABSTRACT

The invention relates to a process for the production of chromatography columns or capillaries containing sorbents of monolithic mouldings which can remain directly in their gelation mould after production. This is achieved by the process according to the invention, in which the gelation mould is repeatedly filled with the monomer sol.

5 Claims, No Drawings

METHOD FOR PRODUCING MONOLITHIC CHROMATOGRAPHY COLUMNS

The invention relates to a process for the production of chromatography columns or capillaries containing monolithic sorbents which can remain directly in their gelation mould after production.

Monolithic sorbents are continually increasing in importance in the area of chromatography, in particular HPLC, micro-LC or electrochromatography. They exhibit significantly better mass-transport properties than columns or capillaries containing particulate sorbents. For this reason, columns containing monolithic sorbents can be operated at a higher linear flow rate with the same efficiency.

Monolithic sorbents can be formed on the basis of organic or inorganic polymers. Owing to the different properties of the polymers, different processes are currently employed for the production of chromatography columns based on monolithic sorbents.

Polymers having low shrinkage rates, i.e. soft polymer gels, can be produced directly in the tubes used for chromatography as gelation mould. Hjerten et al. (Nature, 356, pp. 810–811, 1992) describe, for example, monoliths comprising a polyacrylamide material which are produced inside a chromatography tube. Frechet et al. (Anal. Chem., 64, pp. 820–822, 1993) describe the production of polyacrylate materials and polystyrene-divinylbenzene copolymers which become monolithic materials having a macroporous structure in the presence of porogens and, after production, can remain in the mould used.

However, polymers of this type have some disadvantages for chromatography. For example, they frequently have inadequate mechanical stability. Furthermore, the pore distribution of the materials is frequently unfavourable since too many micropores occur. This has an adverse effect on the efficiency and symmetry of the columns. In addition, the materials often exhibit unfavourable swelling behaviour.

Significantly better separation properties are exhibited by monolithic porous inorganic mouldings or, in some cases, highly crosslinked, hard organic polymer gels. However, these materials shrink during production, which means that they cannot be produced directly in the chromatography tubes. The dead space formed would excessively reduce the separation efficiency. In the case of inorganic monoliths produced by a sol-gel process, the shrinkage after ageing is, for example, up to 20% of the initial diameter. The materials therefore have to be removed from the gelation moulds after production and subsequently encased in tightly sealing tubes.

WO 99/38006 and WO 99/50654 disclose processes for the production of capillaries filled with monolithic silica material. This material can remain directly in the capillary after production. However, the methods disclosed therein are only suitable for the production of capillary columns having a relatively small diameter.

The object of the present invention was therefore to provide a process for the production of monolithic chromatography columns in which the sorbent can remain in the gelation mould, i.e. the column tube, after production. The process should be suitable, in particular, for highly shrinking, i.e., for example, inorganic materials and highly crosslinked organic polymers and should enable the filling of column tubes having a diameter of up to 20 cm.

It has been found that the dead space arising due to shrinkage between the gelation mould and monolith can be compensated by carrying out multiple filling with a monomer sol. In this way, the monolith can remain in the original mould and be employed directly for chromatographic separation. Although the gel has a more rigid three-dimensional network after initial ageing compared with the freshly polymerised or gelled material, it has been found that at this stage the gel is still sufficiently reactive to anchor itself with freshly added monomer sol. This takes place through fresh gelation of the monomer sol onto the aged gel.

According to the opinion in textbooks (Iler, R. K. *The chemistry of silica*; John Wiley & Sons, New York, 1979, page 174), homogeneous networks only form at a pH below pH 7 in the case of silica gels. Above this value, the tendency towards the formation of particles is much more pronounced. Accordingly, the production of monoliths from silica gels is also carried out in acidic medium. However, the subsequent ageing must be carried out under alkaline conditions in order that porous structures form. An aged gel therefore has a pH of about 9. It has now been found that multiple filling is also possible in the production of monoliths from silica. The tendency of the monomer sol to form particles in basic medium can be suppressed. In spite of the high pH of the first filling after ageing, a homogeneous network forms during multiple filling if a pH gradient is generated in the freshly aged monoliths through acidification or rinsing of the outer regions.

The added monomer sol binds to the aged gel and forms a homogeneous structure together therewith. The materials formed exhibit good chromatographic separation properties.

The present invention therefore relates to a process for the production of monolithic porous mouldings which completely fill their gelation mould, characterised by the following process steps:

a) provision of a gelation mould;
b) filling of the gelation mould with monomer sol;
c) polymerisation of the monomer solution;
d) ageing of the gel formed in step c) to form pores;
e) filling of the dead space formed in step d), with further monomer sol, and repetition of steps c) to d), whereby step e) can be carried out one or more times.

In a preferred embodiment, the monolithic porous mouldings are produced using a sol-gel process in which, in step e), a pH gradient is firstly formed on the surface of the aged gel in order that the monomer sol subsequently introduced bonds homogeneously to the already aged gel.

In a further preferred embodiment, the monomer sol subsequently introduced in step e) differs in composition from the monomer sol from step b).

In a preferred embodiment, the gelation mould provided in step a) has an internal diameter of between 1 mm and 100 mm.

The present invention also relates to monolithic porous mouldings which are polymerised into their gelation mould and consist, at least in the core, of porous monolithic material which shrinks on ageing, which can be produced by the process according to the invention.

The present invention relates to the use of the mouldings according to the invention in the gelation mould for the chromatographic separation of at least two substances.

The process according to the invention is suitable for the production of porous monolithic mouldings from monomer sols which shrink during the production process.

Various processes known to the person skilled in the art, such as processes for, for example, free-radical polymerisation or sol-gel processes, can be employed for the production of the mouldings. The solutions which comprise the starting substances for the production of the monoliths are, for the purposes of the invention, referred to as monomer sol, irrespective of the manner in which they are polymerised or gelled.

The process according to the invention is particularly suitable for the production of inorganic porous monolithic mouldings by a sol-gel process. WO 95/03256 and particularly WO 98/29350 disclose processes which are preferred in accordance with the invention for the production of inorganic monolithic mouldings by a sol-gel process. These materials contain mesopores having a diameter of between 2 and 100 nm and macropores having a mean diameter of greater than 0.1 μm and are thus particularly suitable for chromatographic use.

These mouldings can be produced, for example, by hydrolysing silicon alkoxide in a gelation mould under acidic conditions in the presence of a pore-forming phase, for example an aqueous solution of an organic polymer, to give a porous gel body, and then separating off the pore-forming substance and firing the gel. The subsequent ageing of the gel, in particular, causes a change in the gel structure and shrinkage of the gel. This results in the formation of a dead space between the gelation mould and the moulding.

In the process according to the invention, the dead space between the gelation mould and moulding is filled with monomer sol. The gelation mould with moulding and monomer sol is then re-subjected to the various steps of a production process, as described, for example, in WO 95/03256 or WO 98/29350. In order that the monomer sol subsequently introduced bonds as homogeneously as possible to the monolith already present, the basic pH produced by the ageing is preferably compensated by the creation of a pH gradient.

For the purposes of the invention, the phrase "creation of a pH gradient" is taken to mean that the pH on at least the outside of the aged gel bodies is restored to a value equal to or preferably less than pH 7. The pH is preferably adjusted to the pH of the monomer sol to be used subsequently. It is just as possible, but not necessary, to set the entire moulding to this pH. The pH gradient can be established, for example, by washing with water or preferably with an acid or a buffer having a corresponding pH.

Shrinkage of the added gel naturally also occurs during the second ageing. For this reason, it may be necessary to add monomer sol one or more further times, to gel this to completion and to carry out ageing again.

After the gelation mould in which the polymerisation has been carried out has been sufficiently filled with the moulding and the dead space formed by the shrinkage has been filled, a moulding is obtained which is suitable for chromatographic separations and can remain directly in its gelation mould.

It should be noted for the process according to the invention that homogeneous mouldings are only formed if the monomer sol has the same composition during each addition and the gelling and ageing are also carried out under comparable conditions. If a monomer sol having a different composition is selected for filling the dead space, mouldings are produced whose core differs from the outer regions introduced later, for example in terms of pore distribution. However, homogeneous mouldings are preferred for chromatographic separations.

The following compositions, for example, thus arise for mouldings produced in accordance with the invention:
1. mixture of a porous monolith (inside) with a second porous layer (outside) (of the same type);
2. mixture of a porous monolith (inside) with a second, non-porous layer (outside);
3. mixture of a porous inorganic monolith (inside) with a second porous, organic polymer layer (outside);
4. mixture of a porous inorganic monolith with a second, non-porous, organic polymer layer.

For the purposes of the present invention, porous monolithic mouldings accordingly also include mouldings whose inner part consists of a porous material and whose outer layer consists of a non-porous material.

It is thus also possible to combine different production processes. For example, the first, inner moulding can be produced by the sol-gel process outlined above, while the outer layer formed during subsequent introduction is produced by free-radical polymerisation.

For the production of an inorganic monolith having a porous inner structure and non-porous outer layer, the inner structure can be produced, for example, by the sol-gel process described above, while the outer layer is produced starting from monomer sols comprising pure tetramethoxysilane with acid or water or alternatively from monomer sols with ormocers (polysilicic acids or polysiloxanes).

For the purposes of the invention, the term "gelation mould" is taken to mean the mould into which the monolithic mouldings are polymerised completely, i.e. with an accurate fit with no dead space, during production according to the invention. Since the mouldings polymerised-in in accordance with the invention are preferably employed as separation columns for chromatography, the gelation mould simultaneously represents the cladding of the chromatography column. In accordance with the invention, it is no longer necessary to remove the mouldings from the gelation mould for chromatographic use and to provide them with a new cladding.

The gelation mould therefore typically has a size and shape which are conventional for capillaries, analytical or preparative chromatography columns.

It can consist of metal or preferably of plastic, ceramic, glass or other silica materials, such as, for example, fused silica. The person skilled in the art is able to make a selection from these materials on the basis of the reaction conditions and the reactants employed.

For the purposes of the invention, the phrase "polymerised-in completely, i.e. with an accurate fit with no dead space" means that the gelation mould is filled by the moulding in such a way that the chromatographic separation efficiency is no longer impaired by cavities formed in the peripheral regions due to shrinkage processes. The ends of the gelation mould can of course be provided with stoppers or holders of another type in the process according to the invention, so that the monolith does not terminate precisely with the gelation mould after polymerisation-in and removal of the stoppers. Projection of the gelation mould at the ends may be advantageous, in particular for the introduction of filter or sealing elements or for the connection of eluent feed and discharge lines. Accordingly, a gelation mould completely filled in accordance with the invention with monolithic sorbent over the cross section of the gelation mould can also have recesses at the ends.

The process according to the invention can be employed for the production of chromatography columns having internal diameters of from 200 μm to 200 mm, preferably between 1 mm and 100 mm. In the case of thin tubes or capillaries having a diameter of up to 5 mm, it is usually sufficient to fill the dead space formed after the first ageing once with fresh monomer sol. In the case of thicker tubes, subsequent filling three or four times may be necessary.

For use of the mouldings according to the invention polymerised into the gelation mould for chromatography purposes, the gelation mould is usually provided with the corresponding filter or sealing elements and connections for eluent.

With the aid of the process according to the invention, it is possible for the first time to produce monolithic homogeneous porous mouldings which completely fill their gelation mould. The mouldings can remain in the gelation mould for chromatography purposes and exhibit just as homogeneous a pore structure and just as good separation efficiencies on use of uniform monomer solutions as subsequently clad mouldings produced without multiple filling. The process according to the invention will therefore considerably simplify the production of monolithic mouldings for chromatography purposes.

Capillaries produced by the process according to the invention exhibit on average significantly better separation efficiencies than capillaries from the prior art. The reason for this is that dead spaces which occur unnoticed due to shrinkage processes can easily be compensated.

Furthermore, the process according to the invention offers the possibility of producing composite materials by subsequent filling with a different monomer sol. These materials can have different properties depending on the nature of the inner monolith and the outer layer.

Even without further details, it is assumed that a person skilled in the art will be able to utilise the above description in the broadest scope. The preferred embodiments and examples should therefore be regarded merely as descriptive disclosure which is absolutely not limiting in any way.

The complete disclosure content of all applications, patents and publications mentioned above and below, in particular the corresponding application DE 100 28 447, filed on 14 Jun. 2000, is incorporated into this application by way of reference.

EXAMPLES

1.

5 ml of tetramethoxysilane (TMOS) are added to a solution of 0.7 g of polyethylene glycol 10,000 in 10 ml of 0.001 molar acetic acid, and the reaction mixture is stirred at 40° C. for hydrolysis. After a few minutes, a clear solution forms, which, after stirring for 20 minutes at 40° C., is transferred into a Superformance® glass column (Merck KGaA, Germany) having an internal diameter of 5 cm. After 40 minutes under thermostatted conditions (40° C.), the reaction solution solidifies. After the gel formed has aged for 20 hours at constant temperature, shrinkage of the monolith of more than 10% can be established.

Owing to the interspace formed between the monolith and the column wall, it is not possible to employ the monolith directly for use as separating material.

This also becomes clear from the fact that it is readily possible to remove the monolith from the glass tube. For further ageing, it is stored in a plastic dish for 72 hours at 40° C. in 0.1 molar ammonia solution, which is replaced every 24 hours. The pH of the ammonia solution is about 10.

In order to prepare the moist rod for a surface reaction, the outer surface of the monolith is stored in 0.001 molar acetic acid for 1 hour for pH modification and immediately fixed centred in the Superformance® column having an internal diameter of 5 cm. The interspace between monolith and glass wall is filled with a solution prepared as already described above, and allowed to gel at 40° C. Owing to the same pH in the outer region of the first monolith, the gel which forms is able to bond to the surface and form a new compact rod. This monolith can no longer be removed from the glass tube after further ageing at 40° C. for 20 hours. For ageing, the glass column filled with the monolith is stored for 72 hours at 40° C. in a plastic dish in 0.1 molar ammonia solution (the pH is about 10) which is replaced every 24 hours. After this time, the flexible end pieces of the Superformance® column are twisted as far as the ends of the monolith in the interior of the glass body, and the porous monolith is rinsed free from residues with water at a flow rate of 0.5 ml/minute.

2.

5 ml of tetramethoxysilane (TMOS) are added to a solution of 0.7 g of polyethylene glycol 10,000 in 10 ml of 0.001 molar acetic acid, and the reaction mixture is stirred at 40° C. for hydrolysis. After a few minutes, a clear solution forms, which, after stirring for 20 minutes at 40° C., is transferred into a Superformance® glass column (Merck KGaA) having an internal diameter of 5 cm. After 40 minutes under thermostatted conditions (40° C.), the reaction solution solidifies. After the gel formed has aged for 20 hours at constant temperature, shrinkage of the monolith of more than 10% can be established.

Owing to the interspace formed between the monolith and the column wall, it is not possible to employ the monolith directly for use as separating material.

For further ageing, the flexible end pieces of the Superformance® column are twisted until just before the ends of the monolith in the interior of the glass body, and the gap between monolith and glass wall is filled with 0.1 molar ammonia solution with the aid of a pump and stored at 40° C. for 72 hours. The 0.1 molar ammonia solution is replaced every 24 hours. The pH of the ammonia solution is about 10. In order to prepare the moist rod for a surface reaction, 0.001 molar acetic acid is pumped into the gap for pH modification and left to stand for one hour at 40° C.

After this time, a solution prepared as already described above is pumped into the interspace between monolith and glass wall and allowed to gel at 40° C. It should be ensured here that no reaction solution remains in the pump hoses. Owing to the same pH in the outer region of the first monolith, the gel which forms is able to bond to the surface and form a new compact rod. The rod can no longer be removed from the glass tube after ageing at 40° C. for 20 hours. For further ageing, the adjustable end pieces of the Superformance® column are twisted as far as the ends of the monolith in the interior of the glass body, and 20 ml of 0.1 molar ammonia solution (the pH is about 10) are slowly pumped through the porous monolith at 40° C. for further ageing. The pump is then stopped, and the solution is left in the pores of the monolith. This operation is repeated every 24 hours. The monolith is subsequently rinsed free from residues with water at a flow rate of 0.5 ml/minute.

The invention claimed is:

1. A process for the production of monolithic porous moldings which completely fill their gelation mold, said process comprising:
   a) provision of a gelation mold;
   b) filling of the gelation mold with monomer sol;
   c) polymerization of monomer solution;
   d) ageing of gel formed in c) to form pores;
   e) forming a pH gradient on the aged gel, filling of dead space formed in d), with further monomer sol after forming the pH gradient, and repetition of steps c) to d), where e) is carried out sufficient times so as to produce there from monolithic porous moldings.

2. A process according to claim 1, wherein in (e) a pH gradient is formed on the surface of the aged gel formed in (d) by acidification or rinsing of outer regions of the aged gel.

3. The process according to claim 1, wherein the monomer sol subsequently introduced in e) differs in composition from the monomer sol from b).

4. The process according to claim 1, wherein the gelation mould provided in a) has an internal diameter of between 1 mm and 100 mm.

5. A process for the chromatographic separation of at least two substances, comprising preparing a monolithic porous molding according to claim 1, and employing said molding in a chromatographic column under chromatographic separation conditions in the presence of said at least two substances.

* * * * *